(12) United States Patent
Kabu et al.

(10) Patent No.: US 9,493,386 B2
(45) Date of Patent: Nov. 15, 2016

(54) METHOD FOR SUPPLYING REACTION GASES IN CATALYTIC VAPOR PHASE OXIDATION PROCESS

(75) Inventors: Yasuhiro Kabu, Huizhou (JP);
Yoshimasa Ando, Huizhou (JP);
Yoshiyuki Taniguchi, Yokohama (JP)

(73) Assignee: MITSUBISHI RAYON CO., LTD., Tokyo (JP)

( * ) Notice: Subject to any disclaimer, the term of this patent is extended or adjusted under 35 U.S.C. 154(b) by 1837 days.

(21) Appl. No.: 10/564,503

(22) PCT Filed: Jul. 9, 2004

(86) PCT No.: PCT/JP2004/009826
§ 371 (c)(1),
(2), (4) Date: Jan. 13, 2006

(87) PCT Pub. No.: WO2005/005344
PCT Pub. Date: Jan. 20, 2005

(65) Prior Publication Data
US 2006/0166365 A1    Jul. 27, 2006

(30) Foreign Application Priority Data

Jul. 14, 2003 (JP) .................................. 2003-274161

(51) Int. Cl.
*G01N 35/08* (2006.01)
*C07C 45/35* (2006.01)

(52) U.S. Cl.
CPC .............. *C07C 45/35* (2013.01); *Y10T 436/12* (2015.01)

(58) Field of Classification Search
USPC ............................. 436/55; 422/188; 562/534
See application file for complete search history.

(56) References Cited

U.S. PATENT DOCUMENTS 4,954,650 A * 9/1990 Abe et al. ...................... 562/534
6,057,482 A * 5/2000 Okada et al. .................. 568/705

(Continued)

FOREIGN PATENT DOCUMENTS

DE 199 02 562 A1 7/2000
JP 11-80052 3/1999

(Continued)

OTHER PUBLICATIONS

Edited by Kagaku Daijiten Henshu Iinkai 'Kagaku Daijiten 7', Kyoritsu Shuppan Co., Ltd., Showa 37 Nen 8 Gatsu 5 Nichi, $1^{st}$ edition, $2^{nd}$ print, pp. 59 to 60.

Edited by CSJ: The Chemical Society of Japan, 'Kagaku Binran Oyo Hen', Maruzen Co., Ltd., Showa 50 Nen 6 Gatsu 10 Nichi, Revised edition No. 2, $2^{nd}$ print, pp. 1609 to 1611.

(Continued)

*Primary Examiner* — Robert Xu
(74) *Attorney, Agent, or Firm* — Oblon, McClelland, Maier & Neustadt, L.L.P.

(57) ABSTRACT

A method for supplying reaction gases in which at least a material to be oxidized and a gas containing molecular oxygen are mixed and the resultant mixture is supplied to a catalytic gas-phase oxidation reactor, characterized in that, a feed rate of the material to be oxidized and a feed rate of the gas containing molecular oxygen are adjusted so that when a composition of a gas at the inlet of the catalytic gas-phase oxidation reactor is changed from a composition A point [the concentration of the material to be oxidized: $R(a)$, and the concentration of oxygen: $O(a)$] represented by plotting a concentration of the material to be oxidized and a concentration of oxygen in the gas at said inlet to a composition B point [$R(b)$ and $O(b)$] [the composition A point and the composition B point are compositions outside an explosion range, and $R(a) \neq R(b)$ and $O(a) \neq O(b)$], compositions on the way of the change from the composition A point to the composition B point fall outside the explosion range.

12 Claims, 5 Drawing Sheets

(56) References Cited

U.S. PATENT DOCUMENTS

| | | |
|---|---|---|
| 6,410,785 B1 | 6/2002 | Zehner et al. |
| 2001/0009773 A1* | 7/2001 | Bockel-Macal et al. ........ 436/55 |
| 2004/0015012 A1* | 1/2004 | Hammon et al. ............. 562/532 |
| 2004/0116746 A1* | 6/2004 | Ono et al. .................... 564/267 |

FOREIGN PATENT DOCUMENTS

| | | | |
|---|---|---|---|
| JP | 2002-53519 | | 2/2002 |
| JP | WO02068378 | * | 9/2002 |
| JP | 2002-356450 | | 12/2002 |

OTHER PUBLICATIONS

Edited by CSJ: The Chemical Society of Japan, 'Kagaku Binran Oyo Hen', Maruzen Co., Ltd., Heisei 15 Nen 1 Gatsu 30 Nichi, $6^{th}$ edition, pp. 378 to 382.

"Chemical Dictionary 7", edited by Chemical Dictionary Editorial Board, published by Kyoritsu Shupppan Co Ltd, 1989, pocket edition 32th, pp. 59-60 (reference previously submitted, filing partial English translation only).

"Handbook of Chemistry, Applied Chemistry", edited by Chemical Society of Japan, published by Maruzen Co., Jan. 30, 2003, 6th edition, pp. 378-382 (reference previously submitted, filing partial English translation only).

* cited by examiner

Concentration of Material to be Oxidized in Gas at Inlet (%) →

Concentration of Material to be Oxidized in Gas at Inlet (%) →

METHOD FOR SUPPLYING REACTION GASES IN CATALYTIC VAPOR PHASE OXIDATION PROCESS

TECHNICAL FIELD

The present invention relates to a method for supplying reaction gases in a catalytic gas-phase oxidation reaction in which a material to be oxidized and a gas containing molecular oxygen are mixed and the resultant mixture is supplied to a catalytic gas-phase oxidation reactor and subjected to a catalytic gas-phase oxidation reaction, and when the composition of a gas at the inlet of the catalytic gas-phase oxidation reactor is changed, it can be performed safely while bringing out the maximum capability of the production process.

BACKGROUND ART

So far, a method for supplying reaction gases in a catalytic gas-phase oxidation process in which a material to be oxidized and a gas containing molecular oxygen are mixed and the resultant mixture is supplied to a catalytic gas-phase oxidation reactor and subjected to a catalytic gas-phase oxidation reaction has been known. For example, a method of producing methacrolein by reacting isobutylene and oxygen and a method of producing methacrylic acid by reacting methacrolein and oxygen are exemplified (cf. Japanese Patent Application, First Publication No. 2000-356450).

In the case of mixing a material to be oxidized and a gas containing molecular oxygen and performing a catalytic gas-phase oxidation reaction, there is mostly a peculiar explosion range in a compositional range resulting from a combination of a material to be oxidized and molecular oxygen. In the present invention, the explosion range means a compositional range in which the material to be oxidized and oxygen possibly react to cause explosion. Besides an explosion range can be termed as a combustion range.

On the other hand, in the case of a catalytic gas-phase oxidation reaction which produces methacrolein or methacrylic acid by using isobutylene or methacrolein as a material to be oxidized, it is important to avoid giving a catalyst a reducing atmosphere from the view point of the catalyst life, so that the composition of a gas at the inlet of a catalytic gas-phase oxidation reactor tends to become near an explosion range, even though it is outside the explosion range.

Further, in the prior art, an unchanged fixed point in a concentration composition was set up taking a safety into consideration, however, when changing as the occasion demands, especially a concentration composition while continuing an operation, there was no indication about a method of securing safety as for a composition in the course of the change.

DISCLOSURE OF INVENTION

An object of the present invention is to provide a method for supplying reaction gases in a catalytic gas-phase oxidation reaction wherein a compositional change of the reaction gases can be performed safely so as to bring out the maximum capability of a production process even when the reaction is performed under a composition of the reaction gases near an explosion range.

The present invention is a method for supplying reaction gases in a catalytic gas-phase oxidation reaction in which at least a material to be oxidized and a gas containing molecular oxygen are mixed and the resultant mixture is supplied to a catalytic gas-phase oxidation reactor, characterized in that, a feed rate of the material to be oxidized and a feed rate of the gas containing molecular oxygen are adjusted so that when a composition of a gas at the inlet of the catalytic gas-phase oxidation reactor is changed from a composition A point [the concentration of the material to be oxidized: R(a), and the concentration of oxygen: O(a)] represented by plotting a concentration of the material to be oxidized and a concentration of molecular oxygen in the gas at said inlet to a composition B point [the concentration of the material to be oxidized: R(b), and the concentration of oxygen: O(b)] [with a proviso that the composition A point and the composition B point are compositions outside a range in which the material to be oxidized and oxygen possibly react to cause explosion (an explosion range), and R(a)≠R(b) and O(a)≠O(b)], compositions on the way of the change from the composition A point to the composition B point fall outside the explosion range.

In the present invention, feed rates of the material to be oxidized and the gas containing molecular oxygen are adjusted so that when the composition of a gas at the inlet of the reactor is changed from a start composition A point to a target composition B point, it is carried out by changing the composition not along the shortest distance on a plot (that is a straight line connecting the A point with the B point on the plot) but along a roundabout way in order that the composition on the way between the two points falls outside an explosion range, and especially doesn't come up to the explosion range. Consequently, a reaction condition can be changed safely and the maximum capability of a production process can be brought out. In other words, according to the present invention, it is possible to change a compositional condition safely while bringing out the maximum capability of the production process even in the case of performing the reaction with the composition near the explosion range.

BEST MODE FOR CARRYING OUT THE INVENTION

Figure 1:
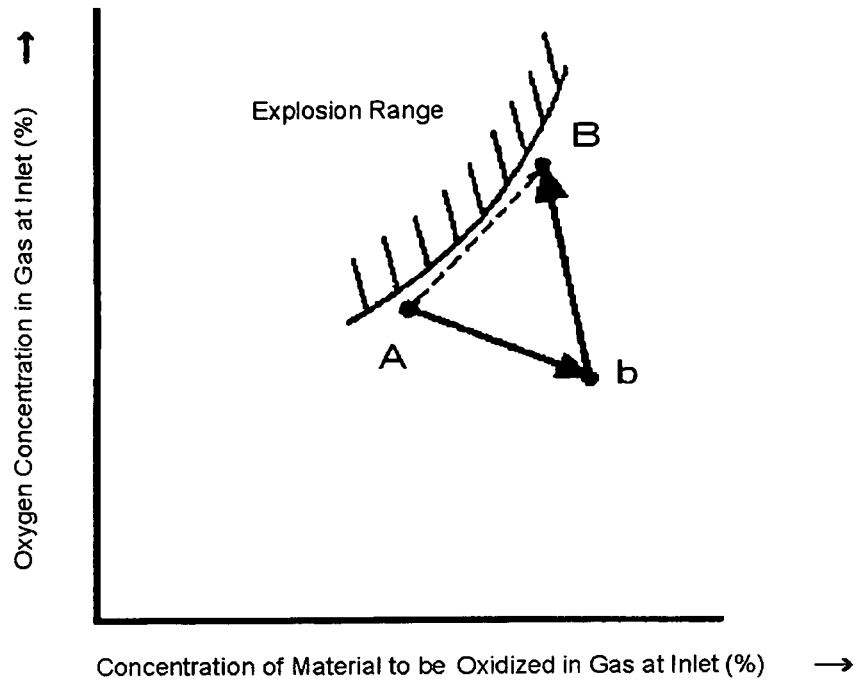
FIG. 1 is a graph plotting compositions of a material to be oxidized and oxygen in a gas at the inlet of a catalytic gas-phase oxidation reactor.

In a method for supplying reaction gases wherein at least a material to be oxidized and a gas containing molecular oxygen are mixed and the resultant mixture is supplied to a catalytic gas-phase oxidation reactor, a change in a composition of reaction gases of a catalytic gas-phase oxidation reaction occurs depending on increase or decrease of an operating load.

A production process using a catalytic gas-phase oxidation reactor usually has a collection step of a reaction product. Therefore, generally, an exhaust gas from the collection step is supplied as a portion of a gas at the inlet of the catalytic gas-phase oxidation reactor to obtain a target composition of the gas at the inlet of the catalytic gas-phase oxidation reactor. Further, other than using the exhaust gas, an inert gas such as nitrogen or water vapor, or a gas obtained after combusting the exhaust gas can be supplied to obtain the target composition of the gas at the inlet of the reactor.

The feed rates of said gases in comparison with the total amount of gases that pass through the process may often be large. Therefore, in such a production process, it is not advisable to increase the supplying amount of a material to be oxidized and oxygen to the catalytic gas-phase oxidation reactor while keeping the composition of a gas at the inlet of the catalytic gas-phase oxidation reactor constant in order to obtain a larger production capacity (high productivity) with the same size of the equipment. This is because to keep the composition of the gas at the inlet of the catalytic gas-phase oxidation reactor constant, it is necessary to increase the supplying amount of the exhaust gas and the like from said collection step and the like, and as a result, the total amount of the gases that pass through the whole process including the catalytic gas-phase oxidation reactor increases excessively to reach the capacity limit earlier.

For this purpose, in a reaction in which a material to be oxidized and a gas containing molecular oxygen are mixed and the resultant mixture is supplied to a catalytic gas-phase oxidation reactor, an increase or a decrease of the operating load to the reactor (productivity) generally cause a change of a composition of a gas at the inlet, and the change of the composition is necessary for an effective and economical operation of the production process and should be performed safely. The present invention is quite useful in such an occasion.

The present invention can be applied generally to a reaction in which a material to be oxidized and oxygen have an explosion range. As the material to be oxidized, propylene, isobutylene, tertiary butyl alcohol, acrolein, methacrolein and the like can be exemplified. Especially, in the case the material to be oxidized is isobutylene, tertiary butyl alcohol or methacrolein, the present invention can be applied effectively. In the present invention, when changing a gas composition just before supplying to the catalytic gas-phase oxidation reactor, a feed rate of the material to be oxidized and a feed rate of the gas containing molecular oxygen are adjusted by taking the explosion range into consideration.

Especially, in the present invention, it is preferable to adjust the feed rates in such a way that one of the feed rates of the material to be oxidized and the gas containing molecular oxygen is adjusted in advance by increasing it or decreasing it to the direction away from the explosion range and then the other feed rate is adjusted by increasing it or decreasing it to reach to the composition B point so that the compositions on the way of the change from the composition A point to the composition B point fall outside the explosion range. Hereinafter, a preferable embodiment is explained by using FIG. 1 and FIG. 2.

FIG. 1 is a graph plotting compositions of a material to be oxidized and oxygen in a gas at the inlet of a catalytic gas-phase oxidation reactor. In this graph, the ordinate axis represents an oxygen concentration (%) in the gas at the inlet, and the abscissa axis represents a concentration of a material to be oxidized (%) in the gas at the inlet. An explosion range showing as an upper range of a curve means that there is a possibility of an explosion when the compositional rate of the material to be oxidized and oxygen comes into this range. In the case of synthesizing a product with a catalytic gas-phase oxidation reaction using a material to be oxidized and oxygen, a composition of a gas at the inlet of the reactor is determined to avoid this range.

As mentioned hereinbefore, in the case of a catalytic gas-phase oxidation reaction producing methacrolein or methacrylic acid by using, especially, isobutylene, tertiary butyl alcohol or methacrolein as a material to be oxidized, the composition of a gas at the inlet of a catalytic gas-phase oxidation reactor tends to become near an explosion range, even though it is outside the explosion range, because it is important to avoid giving a catalyst a reducing atmosphere from the view point of the catalyst life. In the case of synthesizing methacrolein with a catalytic gas-phase oxidation of isobutylene and oxygen, for example, an operation of a normal load is carried out at the A point in FIG. 1 which is near, though outside, the explosion range.

In the case of an operation of a normal load (a normal productivity), it is carried out with a composition of a gas at the inlet represented by the A point in FIG. 1. Further, in the case that an operation above the normal load is necessary, an operating load is increased to the direction of the B point in FIG. 1, that is, to the direction where concentrations of a material to be oxidized and oxygen in the gas at the inlet are increased. A change of the composition of the gas at the inlet from the A point to the B point generally follows the route shown as the dotted line in many cases, but, such a method may not be safe, because the composition may get nearer to the explosion range than it needs and may fall into the explosion range due to the effect of fluctuations of process conditions such as a disorder of a gauge and the like. Moreover, from the practical point of view, following this route changes (increases) the feed rate of a gas containing molecular oxygen such as oxygen gas, air and the like as an oxygen source and the feed rate of the material to be oxidized at the same time, and it is difficult to change the condition by following this dotted line without approaching to the explosion range.

Consequently, in the example shown in FIG. 1, at first, only a feed rate of the material to be oxidized out of the feed rates of a material to be oxidized and a gas containing molecular oxygen is increased and a composition of a gas at the inlet is moved from the A point to the b point. At the b point, the concentration of the material to be oxidized is deservedly increased in comparison with the A point, but the concentration of oxygen is a little decreased as compared with the A point, and the solid line connecting the A point to the intermediate b point is declining. This is because the proportion of oxygen in comparison with the whole gas at the inlet is decreased relatively, as a result of the increase of the feed rate of the material to be oxidized. Subsequently, only the feed rate of the gas containing molecular oxygen out of the feed rates of the material to be oxidized and the gas containing molecular oxygen is increased and the composition of the gas at the inlet is moved to the target B point. Here, the solid line connecting the b point to the B point is inclining, because, with the same reason as the above, the proportion of the material to be oxidized in comparison with the whole gas at the inlet is decreased relatively, as a result of the increase of the feed rate of the gas containing molecular oxygen. According to the above procedure, the risk is reduced in comparison with the route of the compositional change represented by the dotted line and it is possible to change the composition of the gas at the inlet safely.

Figure 2:
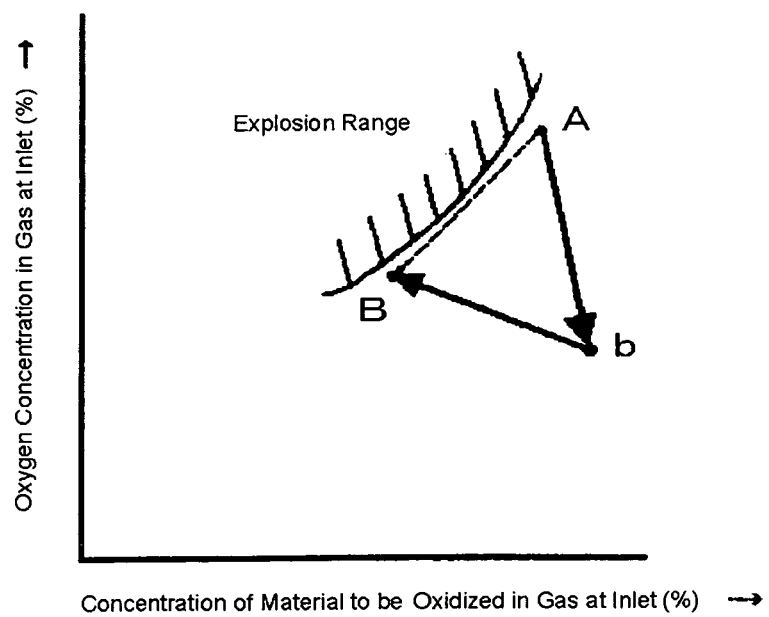
FIG. 2 is a graph plotting compositions of a material to be oxidized and oxygen in a gas at the inlet of a catalytic gas-phase oxidation reactor.

In the next place, an example where a decrease of an operating load is necessary is explained by using FIG. 2. FIG. 2 is, same as in FIG. 1, a graph plotting compositions of a material to be oxidized and oxygen in a gas at the inlet of a catalytic gas-phase oxidation reactor. In this example, changing the composition from the A point to the B point corresponds to decreasing the operating load. A change of the composition of the gas at the inlet from the A point to the B point generally follows the route shown as the dotted line in many cases, but, such a method may cause the composition to get nearer to the explosion range than it needs as mentioned above. Consequently, in the example shown in FIG. 2, only the feed rate of the gas containing molecular oxygen out of the feed rates of the material to be oxidized and the gas containing molecular oxygen is decreased at first and the composition of the gas at the inlet is moved from the A point to the intermediate b point. Subsequently, only the feed rate of the material to be oxidized out of the feed rates of the material to be oxidized and the gas containing molecular oxygen is decreased and the composition of the gas at the inlet is moved from the b point to the B point. According to the above method, the risk is reduced in comparison with the route of the compositional change represented by the dotted line and it is possible to change the composition of the gas at the inlet safely. The reason that the solid line connecting the A point to the b point and the solid line connecting the b point to the B point are sloping is the same as in the case of FIG. 1.

Further, in the case there exists a concentration of a material to be oxidized corresponding to the lowest oxygen concentration of the explosion limit, an example which excludes a method of changing a composition across the above concentration of the material to be oxidized is explained. For example, in the case that isobutylene or methacrolein is used as the material to be oxidized in a catalytic gas-phase oxidation reaction wherein at least the material to be oxidized and a gas containing molecular oxygen are mixed and the resultant mixture is supplied to the catalytic gas-phase oxidation reactor, an explosion range generally has the lowest oxygen concentration of the explosion limit.

Figure 3:
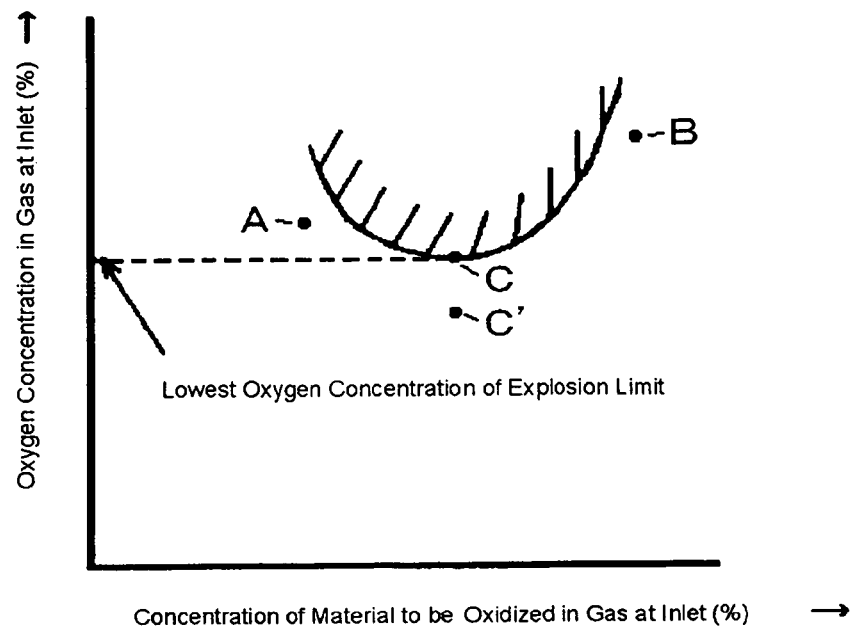
FIG. 3 is a graph plotting compositions of a material to be oxidized and oxygen in a gas at the inlet of a catalytic gas-phase oxidation reactor.

FIG. 3, as well as FIG. 1 and FIG. 2, is a graph plotting compositions of a material to be oxidized and oxygen in a gas at the inlet of a catalytic gas-phase oxidation reactor.

A concentration of the material to be oxidized corresponding to "the lowest oxygen concentration of the explosion limit" in the present invention means a concentration of the material to be oxidized at the minimum composition point such as the C point. In case of changing the composition directly from the A point to the B point across the composition point such as the C point, for example, an explosion range can't be avoided. In such a case, a point outside the explosion range such as the C' point having a composition in which a concentration of the material to be oxidized corresponding to the lowest oxygen concentration of the explosion limit and an oxygen concentration a little lower than the lowest oxygen concentration of the explosion limit may be taken as an intermediate point. Using the point, a composition is changed according to the above method from the A point to the C' point at first, and then the composition is changed from the C' point to the B point according to the above method as well, thus the composition can be changed safely.

In short, the example, as represented by FIG. 3, is the one in which, in the case there exists the composition C point [the concentration of a material to be oxidized: R(c), and the concentration of oxygen: O(c), wherein O(c)<O(a), O(c)<O(b) and R(b)>R(c)>R(a) or R(a)>R(c)>R(b)] of the lowest oxygen concentration of an explosion limit in an explosion range, a feed rate of a material to be oxidized and a feed rate of a gas containing molecular oxygen are adjusted so that the compositions on the way of the change from the composition A point to the composition B point pass through the composition C' point [the concentration of a material to be oxidized: R(c'), and the concentration of oxygen: O(c'), wherein R(c')=R(c), O(c')<O(c)]. In the present invention, such an embodiment is also preferable.

Figure 4:
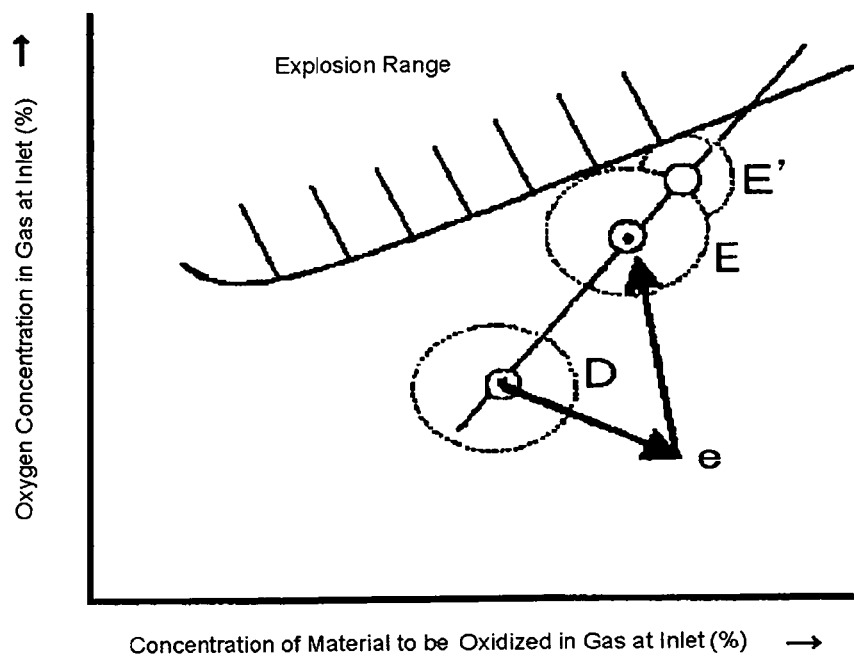
FIG. 4 is a graph plotting compositions of a material to be oxidized and oxygen in a gas at the inlet of a catalytic gas-phase oxidation reactor.

Further, an embodiment to mainly attain a higher productivity in the present invention is explained by using FIG. 4. FIG. 4, as well as FIG. 1 to FIG. 3, is a graph plotting compositions of a material to be oxidized and oxygen in a gas at the inlet of a catalytic gas-phase oxidation reactor. The D point in FIG. 4 represents a composition of the gas at the inlet of the reactor at an operating condition of a standard productivity, that is, at a normal load. And the E point represents a composition of the gas at the inlet at an operating condition of a higher productivity. And the e point represents a similar intermediate point as in the mode of FIG. 1. Further, dotted circles around the D point and the E point qualitatively represent compositional ranges variable in accordance with a real operating facilities or operational states. The size of the radii of these circles can be determined by precision of a control system or by precision of a gauge or an analytical apparatus monitoring an actual composition.

In the catalytic gas-phase oxidation reaction mentioned above, it is necessary to operate avoiding a reducing atmosphere when changing the raw gas composition from the viewpoint of a life of the catalyst used in the oxidation reaction. In order to avoid the reducing atmosphere, it is preferable to maintain a molar ratio of oxygen and a material to be oxidized in the raw gas or to increase a molar ratio of oxygen. The molar ratio corresponds to a slope of the straight line DE in FIG. 4. And an extension of the straight line DE enters into an explosion range as shown in FIG. 4.

In an actual operation, it is necessary to consider a compositional fluctuation within a range of a dotted circle, and the upper limit of the E point when increasing both the concentrations is a point where the dotted circle around the E point contacts with an explosion range. On the other hand, a radius of this circle can be reduced in accordance with the precision of a control system or with the precision of a gauge or an analytical apparatus monitoring an actual composition. Especially in the present invention, the radius of the circle can be reduced by a method of observing all the times a composition of a reaction gas at the inlet with a display such as CRT and the like and preferably connecting the composition with an automatic shutdown system in the case of an unusual access, and as a result, a higher concentration of a composition of the E' point can be adopted safely to attain a higher productivity. That is, in the present invention, it is a very preferable embodiment for attaining a high productivity to show an explosion range and a present compositional point on a display as in FIG. 1 to FIG. 4, and to observe all the times the relation between the explosion range and the compositional point.

The embodiment can be preferably performed by using a program which makes a computer function especially as a means for showing an explosion range on a display and as a means for showing on the display a compositional point which is represented by plotting measured values of concentrations of a material to be oxidized and oxygen in a gas at the inlet of a catalytic gas-phase oxidation reactor as well as the explosion range.

Figure 5:
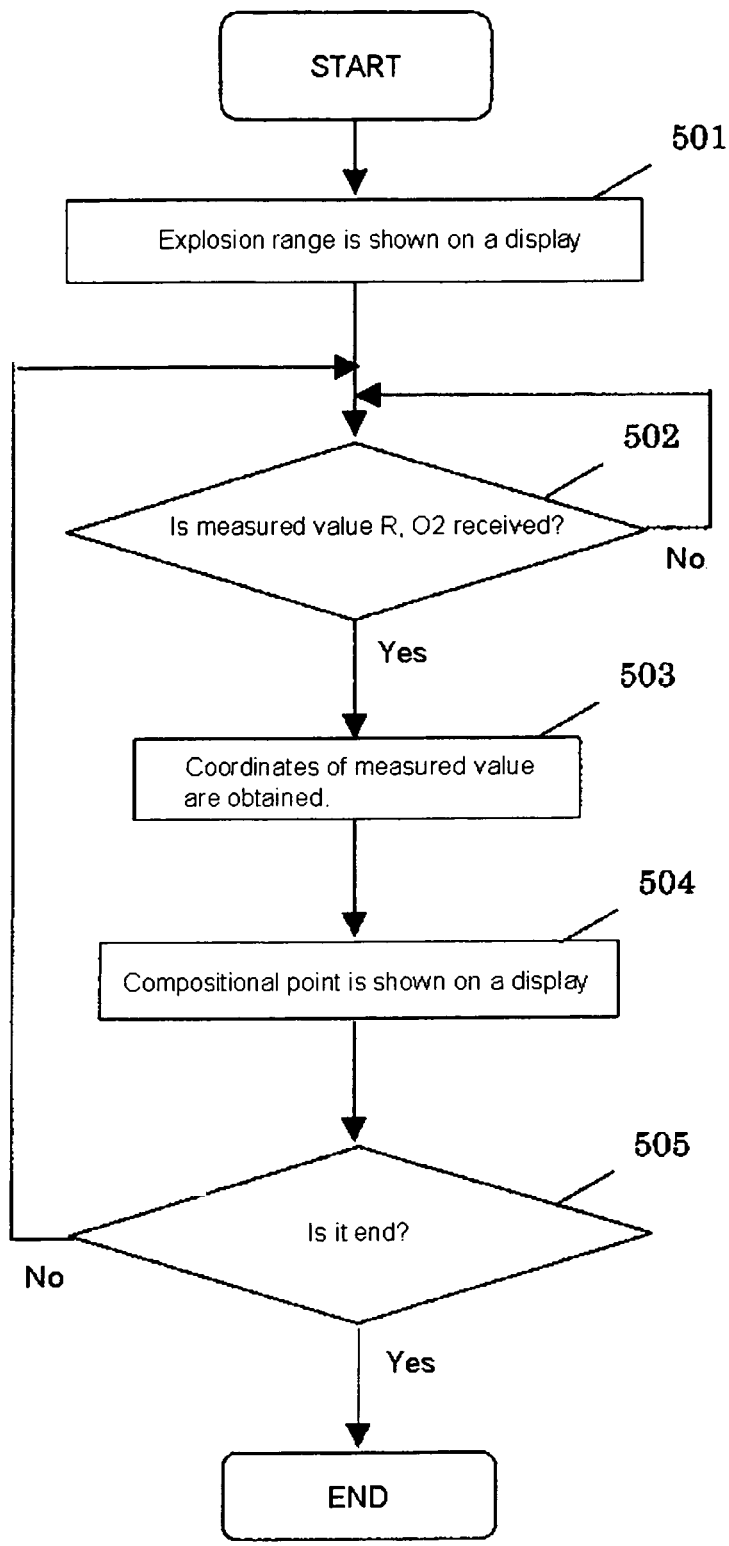
FIG. 5 is a flow chart showing an operating procedure of a computer when using a specific program.

FIG. 5 is a flow chart showing an operating procedure of a computer when using said program. Firstly, based on data of an explosion range of a specific material to be oxidized and oxygen being used, the explosion range is shown on a display (501). Here, the data of the explosion range may be newly input data of a user or already known data previously stored in a program or a computer memory. Secondly, from a measuring device of a concentration of a material to be oxidized (R) and a concentration of oxygen ($O_2$) of a gas at the inlet of the catalytic gas-phase oxidation reactor, a present measured value (R, $O_2$) is received in turn (502). Thirdly, coordinates of the measured value (R, $O_2$) are obtained (503), then the present compositional point is shown together with said explosion range on a display (504). The showing on the display is continued till the end of the operation of the catalytic gas-phase oxidation reaction (505).

So far, each embodiment for carrying out the present invention has been explained, however, the present invention is not limited with these embodiments. For example, in said embodiments, feed rates of a material to be oxidized and a gas containing molecular oxygen are increased or decreased separately, but, both the rates may be changed at the same time if it is possible to adjust the composition at the inlet to be out of the explosion range.

Figure 6:
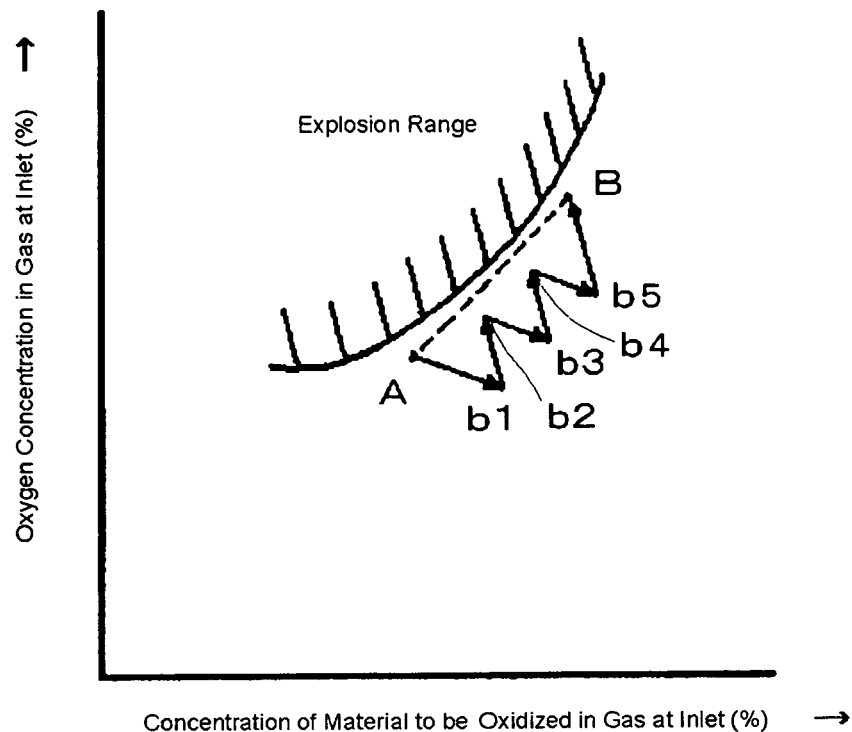
FIG. 6 is a graph plotting compositions of a material to be oxidized and oxygen in a gas at the inlet of a catalytic gas-phase oxidation reactor.

Further, in said embodiments, although a simple change from the composition A point to the composition B point has been explained, it is possible to repeat said method of embodiment plural times in the case that it is necessary to perform a large conditional change. More specifically, it is possible to repeat the method shown in FIG. 1 three times, in other words, to reach the target B point through the five intermediate points b1, b2, b3, b4, b5 shown in FIG. 6.

Hereinafter, the present invention will be entered into details with reference to the following examples.

EXAMPLE 1

At first, isobutylene, oxygen and nitrogen were mixed with various compositional ratios by using an experimental device, and experimental data of compositional points causing explosion and not causing explosion were taken. The experimental data were input into a computer installed with the program mentioned above, and the computer was set to show an explosion range with respect to isobutylene and oxygen on a display.

Figure 7:
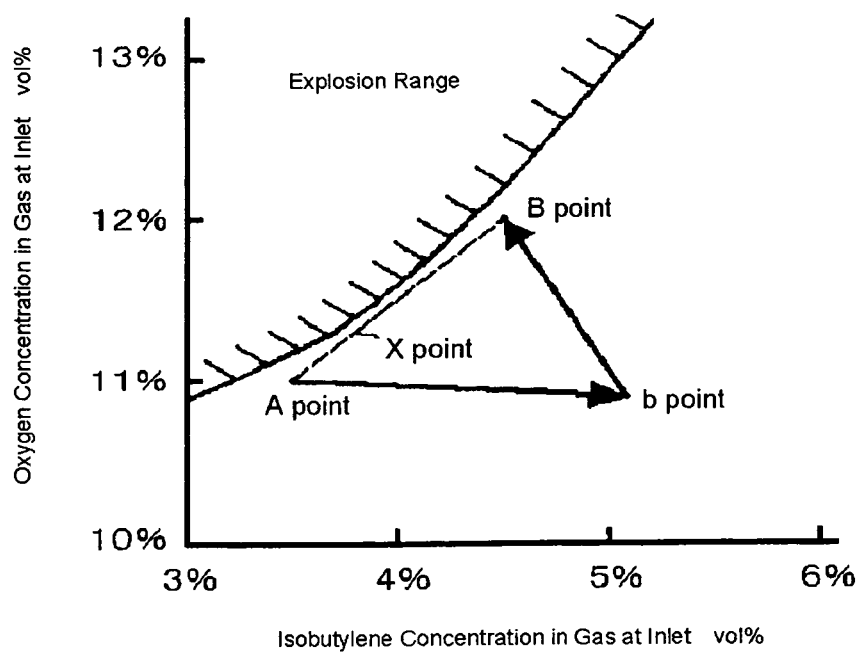
FIG. 7 is a graph plotting compositions of the material to be oxidized and oxygen in the gas at the inlet of the catalytic gas-phase oxidation reactor in Example 1 (and Comparative example 1).

In a production process in which isobutylene and oxygen is subjected to react to produce methacrolein, then isobutylene, air and an exhaust gas from a collection step were mixed and, as shown in FIG. 7, the mixed gas (the A point) adjusted to have isobutylene concentration of 3.5% by volume and oxygen concentration of 11% by volume was supplied to the inlet of an oxidation reactor. The exhaust gas from the collection step was used as a gas for dilution in order to adjust the composition. From this state, an operating load was changed to isobutylene concentration of 4.5% by volume and oxygen concentration of 12% by volume (the B point), without changing a feed rate of the gas for dilution. When the change was performed, a feed rate of isobutylene was increased at first to isobutylene concentration of 5.09% by volume and oxygen concentration of 10.82% by volume (the b point), and then a feed rate of air was increased to isobutylene concentration of 4.5% by volume and oxygen concentration of 12% by volume, while monitoring a graph of an explosion range and a compositional point shown on a display as shown in FIG. 7, and a target load change was performed. The load change was performed safely and didn't get near to the explosion range, as shown in FIG. 7.

EXAMPLE 2

At first, methacrolein, oxygen and nitrogen were mixed with various compositional ratios by using an experimental device, and experimental data of compositional points causing explosion and not causing explosion were taken. The experimental data were input into a computer installed with the program mentioned above, and the computer was set to show an explosion range with respect to methacrolein and oxygen on a display.

Figure 8:
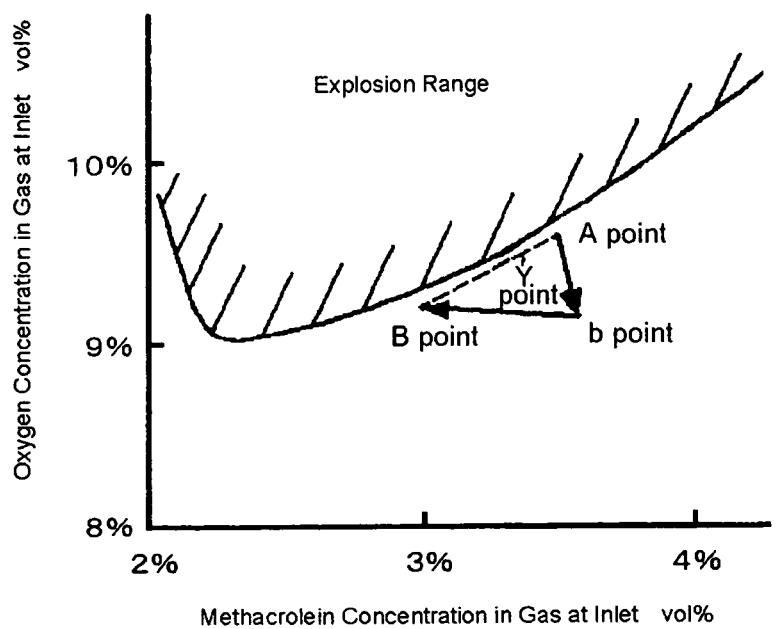
FIG. 8 is a graph plotting compositions of the material to be oxidized and oxygen in the gas at the inlet of the catalytic gas-phase oxidation reactor in Example 2 (and Comparative example 2).

In a production process in which methacrolein and oxygen is subjected to react to produce methacrylic acid, then methacrolein, air and an exhaust gas from a collection step were mixed and, as shown in FIG. 8, the mixed gas (the A point) adjusted to have methacrolein concentration of 3.5% by volume and oxygen concentration of 9.65% by volume was supplied to the inlet of an oxidation reactor. The exhaust gas from the collection step was used as a gas for dilution in order to adjust the composition. From this state, an operating load was changed to methacrolein concentration of 3% by volume and oxygen concentration of 9.23% by volume (the B point), without changing a feed rate of the gas for dilution. When the change was performed, a feed rate of air was decreased at first to methacrolein concentration of 3.65% by volume and oxygen concentration of 9.17% by volume (the b point), and then a feed rate of methacrolein was decreased to methacrolein concentration of 3% by volume and oxygen concentration of 9.23% by volume, while monitoring a graph of an explosion range and a compositional point shown on a display as shown in FIG. 8, and a target load change was performed. The load change was performed safely and didn't get near to the explosion range, as shown in FIG. 8.

COMPARATIVE EXAMPLE 1

In a production process same as in Example 1, the mixed gas was adjusted to have isobutylene concentration of 3.5% by volume and oxygen concentration of 11% by volume (the A point). From this state, the composition was tried to change, by increasing a feed rate of isobutylene and a feed rate of air at the same time, without changing a feed rate of the gas for dilution, to isobutylene concentration of 4.5% by volume and oxygen concentration of 12% by volume (the B point), following the dotted line in FIG. 7. However, in the course of the compositional change, the composition was liable to come into the explosion range in the vicinity of the X point, so, thereafter the operation was discontinued.

COMPARATIVE EXAMPLE 2

In a production process same as in Example 2, the mixed gas was adjusted to have methacrolein concentration of 3.5% by volume and oxygen concentration of 9.65% by volume (the A point). From this state, the composition was tried to change, by decreasing a feed rate of methacrolein and a feed rate of air at the same time, without changing a feed rate of the gas for dilution, to methacrolein concentration of 3% by volume and oxygen concentration of 9.23% by volume (the B point), following the dotted line in FIG. 8.

However, in the course of the compositional change, the feed rate of air fluctuated and the composition was liable to come into the explosion range in the vicinity of the Y point, so, thereafter the operation was discontinued.

The invention claimed is:
1. A method for supplying reaction gases in a catalytic gas-phase oxidation reaction in which at least a material to be oxidized and a gas containing molecular oxygen are mixed and the resultant mixture is supplied to a catalytic gas-phase oxidation reactor,
wherein a feed rate of the material to be oxidized and a feed rate of the gas containing molecular oxygen are adjusted, without shutting off a feed, so that when a composition of a gas at the inlet of the catalytic gas-phase oxidation reactor is changed from a reactive composition A point, which is the concentration of the material to be oxidized: R(a), and the concentration of oxygen: O(a) represented by plotting a concentration of the material to be oxidized and a concentration of oxygen in the gas at said inlet to a reactive composition B point, which is the concentration of the material to be oxidized: R(b), and the concentration of oxygen: O(b), with a proviso that the composition A point and the composition B point are compositions outside a range in which the material to be oxidized and oxygen possibly react to cause explosion, which range is an explosion range, and R(a)≠R(b) and O(a)≠O(b), compositions on the way of the change from the composition A point to the composition B point fall outside the explosion range,
wherein the material to be oxidized is isobutylene, tertiary butyl alcohol or methacrolein,
wherein one of the feed rates of the material to be oxidized and the gas containing molecular oxygen is adjusted in advance by increasing it or decreasing it to the direction away from the explosion range and then the other feed rate is adjusted by increasing it or decreasing it to reach to the composition B point so that the compositions on the way of the change from the composition A point to the composition B point fall outside the explosion range.
2. The method for supplying reaction gases in the catalytic gas-phase oxidation reaction according to claim 1, wherein in the case there exists the composition C point [the concentration of the material to be oxidized: R(c), and the concentration of oxygen: O(c), wherein O(c)<O(a), O(c)<O(b) and R(b)>R(c)>R(a) or R(a)>R(c)>R(b)] of the lowest oxygen concentration of an explosion limit in the explosion range, a feed rate of the material to be oxidized and a feed rate of the gas containing molecular oxygen are adjusted so that compositions on the way of the change from the composition A point to the composition B point pass through the composition C' point [the concentration of the material to be oxidized: R(c'), and the concentration of oxygen: O(c'), wherein R(c')=R(c) and O(c')<O(c)].
3. The method for supplying reaction gases in the catalytic gas-phase oxidation reaction according to claim 1, wherein the range in which the material to be oxidized and oxygen possibly react to cause explosion, which range is an explosion range, and a present compositional point represented by plotting concentrations of the material to be oxidized and oxygen in the gas at the inlet of the catalytic gas-phase oxidation reactor are shown and monitored on a display.
4. The method of supplying reaction gases in the catalytic gas-phase oxidation reaction according to claim 1, wherein the material to be oxidized is isobutylene.
5. The method of supplying reaction gases in the catalytic gas-phase oxidation reaction according to claim 1, wherein the material to be oxidized is tertiary butyl alcohol.
6. The method of supplying reaction gases in the catalytic gas-phase oxidation reaction according to claim 1, wherein the material to be oxidized is methacrolein.
7. The method of supplying reaction gases in the catalytic gas-phase oxidation reaction according to claim 1, wherein the change from the composition A point to the composition B point is carried out through multiple composition points.
8. The method of supplying reaction gases in the catalytic gas-phase oxidation reaction according to claim 1, wherein R(a)≠O and O(a)≠O.
9. The method of supplying reaction gases in the catalytic gas-phase oxidation reaction according to claim 1, wherein the feed rates of the material to be oxidized and the gas containing molecular oxygen are adjusted by changing the composition not along a straight line connecting the reactive composition A point with the reactive composition B point, but along a roundabout way in order that the composition on the way between the reactive composition A point and the reactive composition B point falls outside an explosion range and does not come up to the explosion range.
10. The method of supplying reaction gases in the catalytic gas-phase oxidation reaction according to claim 1, wherein an operating load at the reactive composition B point is above an operating load at the reactive composition A point and the feed rate of the material to be oxidized or the feed rate of the gas containing molecular oxygen is adjusted in advance by increasing it to the direction away from the explosion range and then the other feed rate is adjusted by increasing it to reach the reactive composition B point so that the compositions on the way of change from the composition A point to the composition B point fall outside the explosion range, or
wherein an operating load at the reactive composition B point is below an operating load at the reactive composition A point and the feed rate of the material to be oxidized or the feed rate of the gas containing molecular oxygen is adjusted in advance by decreasing it to the direction away from the explosion range and then the other feed rate is adjusted by decreasing it to reach the reactive composition B point so that the compositions on the way of change from the composition A point to the composition B point fall outside the explosion range.
11. The method of supplying reaction gases in the catalytic gas-phase oxidation reaction according to claim 10, wherein an operating load at the reactive composition B point is above an operating load at the reactive composition A point and the feed rate of the material to be oxidized or the feed rate of the gas containing molecular oxygen is adjusted in advance by increasing it to the direction away from the explosion range and then the other feed rate is adjusted by increasing it to reach the reactive composition B point so that the compositions on the way of change from the composition A point to the composition B point fall outside the explosion range.
12. The method of supplying reaction gases in the catalytic gas-phase oxidation reaction according to claim 10, wherein an operating load at the reactive composition B point is below an operating load at the reactive composition A point and the feed rate of the material to be oxidized or the feed rate of the gas containing molecular oxygen is adjusted in advance by decreasing it to the direction away from the explosion range and then the other feed rate is adjusted by decreasing it to reach the reactive composition B point so that the compositions on the way of change from the composition A point to the composition B point fall outside the explosion range.

* * * * *